US012723043B2

(12) United States Patent
Hirose

(10) Patent No.: US 12,723,043 B2
(45) Date of Patent: Sep. 1, 2026

(54) METHOD FOR PREPARING MORPHINAN DERIVATIVE HAVING DIARYL ETHER SKELETON USING NOVEL COPPER CATALYST

(71) Applicant: NIPPON CHEMIPHAR CO., LTD., Tokyo (JP)

(72) Inventor: Masaaki Hirose, Saitama (JP)

(73) Assignee: NIPPON CHEMIPHAR CO., LTD., Tokyo (JP)

( * ) Notice: Subject to any disclaimer, the term of this patent is extended or adjusted under 35 U.S.C. 154(b) by 681 days.

(21) Appl. No.: 18/023,461

(22) PCT Filed: Aug. 27, 2021

(86) PCT No.: PCT/JP2021/031558

§ 371 (c)(1),
(2) Date: Feb. 27, 2023

(87) PCT Pub. No.: WO2022/045301

PCT Pub. Date: Mar. 3, 2022

(65) Prior Publication Data

US 2023/0312570 A1 Oct. 5, 2023

(30) Foreign Application Priority Data

Aug. 28, 2020 (JP) ................................ 2020-145073

(51) Int. Cl.
*C07D 471/08* (2006.01)
*B01J 23/72* (2006.01)

(52) U.S. Cl.
CPC ............ *C07D 471/08* (2013.01); *B01J 23/72* (2013.01)

(58) Field of Classification Search
CPC ............................... C07D 471/08; B01J 23/72
See application file for complete search history.

(56) References Cited

U.S. PATENT DOCUMENTS 4,709,081 A 11/1987 Héja et al.
2014/0343015 A1 11/2014 Nagase et al.
2016/0122349 A1 5/2016 Nagase et al.
2018/0057493 A1 3/2018 Nagase et al.
2020/0079775 A1 3/2020 Nagase et al.
2021/0040094 A1 2/2021 Nagase et al.
2022/0267327 A1 8/2022 Saito et al.
2022/0289748 A1 9/2022 Hirose

FOREIGN PATENT DOCUMENTS

EP 0 612 730 A1 8/1994
EP 2 774 926 A1 9/2014
WO 2013/035833 A1 3/2013
WO 2014/136305 A1 9/2014
WO 2016/148232 A1 9/2016
WO 2021/015108 A1 1/2021
WO 2021/015109 A1 1/2021

OTHER PUBLICATIONS

Kamellia Nejati, et al., "Diaryl ethers synthesis: Nano-catalysts in carbon-oxygen cross-coupling reactions", RSC Advances, May 23, 2018, vol. 8, No. 34, pp. 19125-19143.
Yoshikazu Watanabe et al., "Design and synthesis of novel δ opioid receptor agonists with an azatricyclodecane skeleton for improving blood-brain barrier penetration", Bioorganic & Medicinal Chemistry Letters, May 26, 2017, vol. 27, No. 15, pp. 3495-3498.
Jee Young Kim et al., "$Cu_2O$ Nanocube-Catalyzed Cross-Coupling of Aryl Halides with Phenols via Ullmann Coupling", European Journal of Inorganic Chemistry, Sep. 21, 2009, vol. 2009, No. 28, pp. 4219-4223.
Laszlo Revesz et al., "Design and Synthesis of Novel Opiate Antagonists with LH-Stimulating Properties", Helvetica Chimica Acta, 1990, vol. 73 (2), pp. 326-336.
J.T.M. Linders et al., "Diels-Alder reaction of 6-demethoxy-β-dihydrotfiebaine with methyl vinyl ketone using microwave heating; preparation and pharmacology of 3-hydroxy-α, α, 17-trimethyl-6 β, 14 β-ethenomorphinan-7 β-methanol, a novel deoxygenated diprenorphine analogue (chemistry of opium alkaloids, part XXV)", Recueil des Travaux Chimiques des Pays-Bas., 1988, vol. 107, pp. 449-454.

(Continued)

*Primary Examiner* — Susanna Moore
(74) *Attorney, Agent, or Firm* — Greenblum & Bernstein, P.L.C.

(57) ABSTRACT

Provided is a method which is for preparing a morphinan derivative having a diaryl ether skeleton represented by general formula (III) (In the formula, $R^1$ represents a hydrogen atom, etc., $R^2$, $R^3$, and $R^4$ are the same or different and each represent a hydrogen atom, or an arbitrary substituent, etc., $R^5$ represent a hydrogen atom, a hydroxy group, etc., $R^{14}$ and $R^{15}$ are the same or different and each represent a hydrogen atom, or an arbitrary substituent, etc.), and in which a phenyl group is introduced into the 4-position phenol of a morphinan derivative through the Ullmann reaction of a system using a monovalent copper compound or a novel catalytic system simultaneously using a monovalent copper compound and zero-valent metallic copper.

(III)

22 Claims, No Drawings

(56) References Cited

OTHER PUBLICATIONS

International Search Report and Written Opinion of the International Searching Authority Issued in International Patent Application No. PCT/JP2021/031558, dated Sep. 28, 2021, along with an English translation thereof.

Yasamut et al., "A modified Cu(0)-Cu(I)-mediated $C_{aryl}$-$C_{aryl}$ Ullmann coupling for the synthesis of biaryls", Tetrahedron 72, 2016, p. 5994-6000.

Waszkielewicz et al. "Design, synthesis, and anticonvulsant activity of some derivatives of xanthone with aminoalkanol moieties", Chemical Biology & Drug Design, vol. 89, No. 3, 2016, pp. 339-352.

Hossian et al., "Carboxyl radical-assisted 1,5-aryl migration through Smiles rearrangement", Organic & Biomolecular Chemistry, vol. 14, No. 41, 2016, pp. 9768-9779.

Szkaradek et al., "Cardiovascular activity of the chiral xanthone derivatives", Bioorganic & Medicinal Chemistry, vol. 23, No. 20, 2015, pp. 6714-6724.

Partial Supplementary European Search Report issued in the corresponding European Patent Application No. 21861722, dated Aug. 22, 2024.

Hu Bingfang (Editor); Organic Synthesis; Beijing Agricultural University Press; 1st edition, Nov. 1992; p. 78; along with English Translation thereof.

Liu Qingjian (Editor); Organic Chemistry; Tongji University Press; vol. 1, 1st edition, Nov. 2018; p. 433; along with English Translation thereof.

Search Report that issued in corresponding Chinese Patent Application No. 202180052290.2, dated Jun. 14, 2025; along with English Translation thereof.

METHOD FOR PREPARING MORPHINAN DERIVATIVE HAVING DIARYL ETHER SKELETON USING NOVEL COPPER CATALYST

TECHNICAL FIELD

The present invention relates to a method for preparing a morphinan derivative having a diaryl ether skeleton in which a phenolic hydroxyl group of a morphinan derivative is converted into a phenol ether bond by Ullmann coupling using a novel copper catalyst.

The present application claims priority based on Japanese Patent Application No. 2020-145073 filed on Aug. 28, 2020, the contents of which are incorporated herein by reference.

BACKGROUND ART

Three subtypes of opioid receptors, μ, δ, and κ, are known, and morphine that exhibits strong affinity for the μ receptor has been used as an analgesic drug for a long time. Though the analgesic action of morphine is strong, morphine is also known to cause adverse events such as dependence formation, respiratory depression, and constipation through this μ receptor.

Meanwhile, an analgesic action via the δ receptor is also known, and the δ receptor agonist is known not to be involved in adverse events seen in morphine.

Thus, presumably, an agonist selective for the δ receptor can become an analgesic drug superior to morphine, and research on the creation thereof is actively conducted. However, there are still no δ receptor agonists approved as therapeutic or prophylactic agents.

Patent Literature 1 and Patent Literature 2 disclose derivatives having excellent δ receptor agonist activity and represented by the following formula.

[Chemical Formula 1]

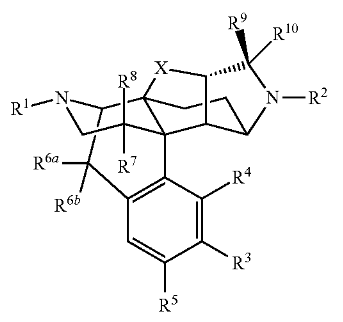

The preparation of these derivatives needs multi-step synthesis, and thus the yield in one reaction and the purity of the target compound obtained by each reaction are desirably high.

For example, paragraph [0025] of Patent Literature 1 discloses a technique in which a phenyl group is introduced into 4-position phenol (b-1) of a morphinan derivative by an Ullmann reaction to form a compound (m), and then an oxygen functional group at the 4-position is removed to form a compound (n).

[Chemical Formula 2]

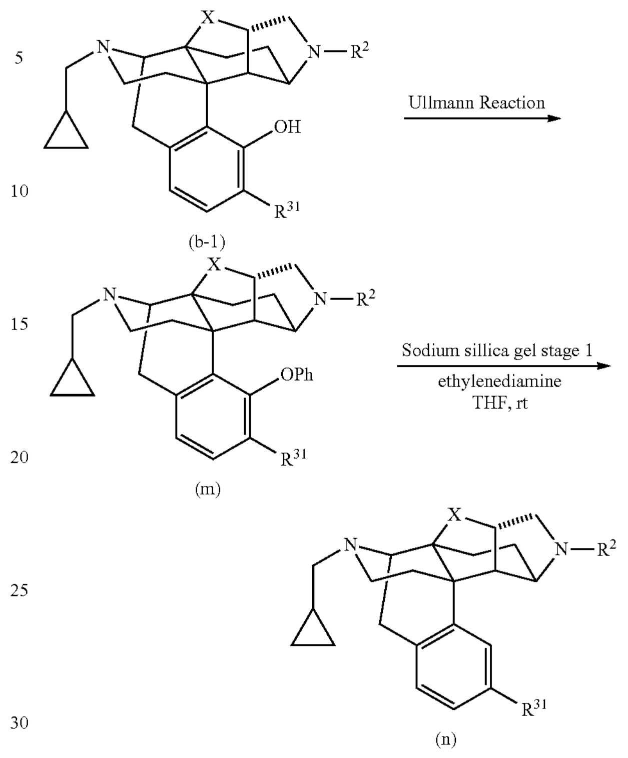

(b-1)

(m)

(n)

Here, in the above Ullmann reaction, a copper powder (zero-valent copper) is used to introduce a phenyl group into a morphinan derivative.

On the other hand, Non Patent Literature 1 discloses a method using divalent copper (copper(II) acetate) in constructing diaryl ether by introducing a phenyl group into a morphinan derivative by an Ullmann reaction.

CITATION LIST

Patent Literature

Patent Literature 1: WO 2013/035833 A
Patent Literature 2: WO 2016/148232 A

Non Patent Literature

Non Patent Literature 1: Helvetica Chimica Acta 1990, 73(2), 326-336

SUMMARY OF INVENTION

Technical Problem

According to Example 2 of Patent Literature 1, when a phenyl group is introduced by an Ullmann reaction, the reaction is not completed even if a copper powder is added in a theoretical equivalent, and there is a problem in reproducibility in which a copper powder needs to be added in the middle of the reaction, and it must be said that the method is unsuitable for industrialization.

Therefore, one object of the present invention is to provide a method for preparing a morphinan derivative having a diaryl ether skeleton, the method being applicable to an industrial preparation method.

Solution to Problem

As a result of intensive studies, the present inventors have found, as a catalytic system for preparing diaryl ether by an Ullmann reaction, a system using a monovalent copper compound that has not been known so far, particularly, a novel catalytic system simultaneously using a monovalent copper compound and zero-valent metallic copper, and have completed the present invention.

That is, according to the present invention, the following invention is provided.

[1]

The present invention relates to a method for preparing a morphinan derivative the method comprising:

reacting a compound represented by the following general formula (I):

[Chemical Formula 3]

(I)

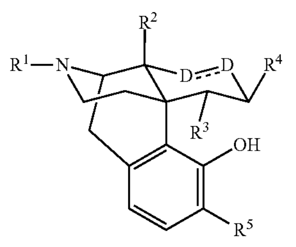

wherein $R^1$ represents a hydrogen atom, a $C_{1-10}$ alkyl group optionally having a substituent, a $C_{3-6}$ cycloalkyl $C_{1-6}$ alkyl group optionally having a substituent, an aralkyl group optionally having a substituent, a heteroarylalkyl group optionally having a substituent, a $C_{3-6}$ cycloalkyl group optionally having a substituent, a $C_{6-10}$ aryl group optionally having a substituent, a heteroaryl group optionally having a substituent, a $C_{2-6}$ alkenyl group optionally having a substituent, or an amino protecting group, $R^2$, $R^3$, and $R^4$ are the same or different and each represent a hydrogen atom or an arbitrary substituent, or with respect to the moiety:

[Chemical Formula 4]

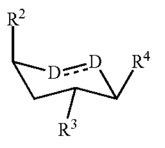

of the general formula (I), $R^2$ and $R^4$ are bonded to each other to represent:

[Chemical Formula 5]

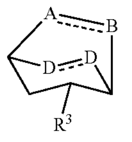

wherein a double line consisting of a solid line and a broken line represents a single bond or a double bond, wherein, when the double line consisting of a solid line and a broken line between A and B is a single bond, then A and B are the same or different and each represent $CR^6R^7$, C═O, or $NR^8$, wherein $R^6$ and $R^7$ are the same or different and each represent a hydrogen atom, —C(═O)—$R^9$, or —$CR^{10}$(OH)—$R^{11}$, and $R^8$ to $R^{11}$ each represent a hydrogen atom or an arbitrary substituent, and when the double line consisting of a solid line and a broken line between A and B is a double bond, then A and B are the same or different and each represent $CR^6$ or N, wherein $R^6$ and $R^9$ to $R^{11}$ each represent the same as mentioned above, and when the double line consisting of a solid line and a broken line between D and D is a single bond, then D represents $CH_2$, and when the double line consisting of a solid line and a broken line between D and D is a double bond, then D represents CH, or $R^2$ to $R^4$ are bonded to each other to represent:

[Chemical Formula 6]

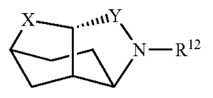

wherein X represents $CH_2$, $NR^8$ ($R^8$ represents a hydrogen atom or an arbitrary substituent), or O, Y represents $CH_2$ or C═O, and $R^{12}$ represents an amino protecting group or an acyl group, and $R^5$ represents a hydrogen atom, a hydroxy group, or —$OR^{13}$ ($R^{13}$ represents a hydroxy protecting group), with a compound represented by the following general formula (II):

[Chemical Formula 7]

(II)

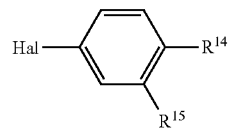

wherein $R^{14}$ and $R^{15}$ are the same or different and each represent a hydrogen atom or an arbitrary substituent, and Hal represents a halogen atom, in an organic solvent in the presence of a base, a monovalent copper compound, and/or zero-valent metallic copper, and the morphinan derivative being represented by the following general formula (III):

[Chemical Formula 8]

(III)

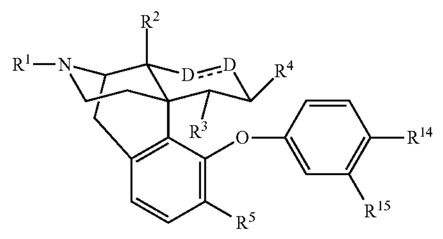

wherein $R^1$ to $R^{15}$, A, B, D, X, and Y each represent the same as mentioned above.

[2]

The present invention relates to the preparation method according to [1] above, wherein the double line consisting of a solid line and a broken line between A and B represents a single bond, A and B are the same or different and each represent $CR^6R^7$, $R^6$ and $R^7$ are the same or different and each represent a hydrogen atom or —C(═O)—$R^9$, $R^9$ represents a $C_{1-10}$ alkyl group, a $C_{1-10}$ alkoxyl group, a $C_{6-10}$ aryl group, or NHBn, the double line consisting of a solid line and a broken line between D and D represents a double bond, and D represents CH.

[3]

The present invention relates to the preparation method according to [1] above, wherein the double line consisting of a solid line and a broken line between A and B represents a single bond, A and B are the same or different and each represent $CR^6R^7$, $R^6$ and $R^7$ are the same or different and each represent a hydrogen atom or —C(═O)—$R^9$, $R^9$ represents a $C_{1-10}$ alkyl group, a $C_{1-10}$ alkoxyl group, a $C_{6-10}$ aryl group, or NHBn, the double line consisting of a solid line and a broken line between D and D represents a single bond, and D represents $CH_2$.

[4]

The present invention relates to the preparation method according to [1] above, wherein the double line consisting of a solid line and a broken line between A and B represents a single bond, A and B are the same or different and each represent $CR^6R^7$, $R^6$ and $R^7$ are the same or different and each represent a hydrogen atom or —$CR^{10}$(OH)—$R^{11}$, $R^{10}$ and $R^{11}$ are the same or different and each represent a hydrogen atom, a $C_{1-10}$ alkyl group, a $C_{6-10}$ aryl group, or a heteroaryl group, the double line consisting of a solid line and a broken line between D and D represents a single bond, and D represents $CH_2$.

[5]

The present invention relates to the preparation method according to claim 1, wherein the general formula (I) is a compound represented by the following general formula (IV):

[Chemical Formula 9]

(IV)

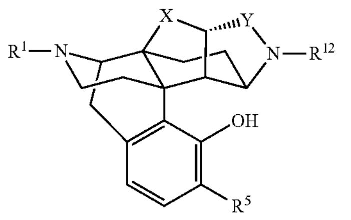

wherein $R^1$ to $R^{13}$, X, and Y each represent the same as mentioned above, and the general formula (III) is a morphinan derivative represented by the following general formula (V):

[Chemical Formula 10]

(V)

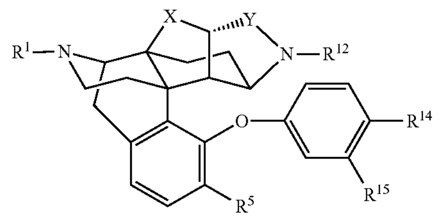

wherein $R^1$ to $R^{15}$, X, and Y each represent the same as mentioned above.

[6]

The present invention relates to the preparation method according to any one of [1] to [5] above, wherein $R^1$ is a methyl group, a cyclopropylmethyl group, a cyclobutylmethyl group, a benzyl group, or an allyl group.

[7]

The present invention relates to the preparation method according to any one of [1] to [5] above, wherein $R^1$ is a cyclopropylmethyl group.

[8]

The present invention relates to the preparation method according to any one of [1] to [5] above, wherein $R^1$ is a methyl group.

[9]

The present invention relates to the preparation method according to any one of [1] to [8] above, wherein $R^5$ is a hydroxy group or —$OR^{13}$ ($R^{13}$ represents a hydroxy protecting group).

[10]

The present invention relates to the preparation method according to any one of [1] to [8] above, wherein $R^5$ is —$OR^{13}$, and $R^{13}$ is a methyl group, a benzyl group, or a tert-butyldimethylsilyl group.

[11]

The present invention relates to the preparation method according to any one of [1] to [8] above, wherein $R^5$ is —$OR^{13}$, and $R^{13}$ is a methyl group.

[12]

The present invention relates to the preparation method according to any one of [1] to [11] above, wherein X is $CH_2$.

[13]

The present invention relates to the preparation method according to any one of [1] to [12] above, wherein Y is $CH_2$.

[14]

The present invention relates to the preparation method according to any one of [1] to [13] above, wherein $R^{12}$ is a benzyl group.

[15]

The present invention relates to the preparation method according to any one of [1] to [13] above, wherein $R^{12}$ is pyridine 1-oxide carbonyl optionally substituted with 1 to 4 substituents selected from a $C_{1-10}$ alkyl group substituted with 1 to 3 fluorines or an unsubstituted $C_{1-10}$ alkyl group, or pyridin-2(1H)-one carbonyl optionally substituted with 1 to 4 substituents selected from a $C_{1-10}$ alkyl group substituted with 1 to 3 fluorines or an unsubstituted $C_{1-10}$ alkyl group.

[16]

The present invention relates to the preparation method according to [5] above, wherein $R^5$ is $—OR^{13}$, $R^{13}$ is a methyl group or another hydroxy protecting group, and X represents $CH_2$ or O.

[17]

The present invention relates to the preparation method according to [5] above, wherein $R^1$ is a cyclopropylmethyl group or a methyl group, and X represents $CH_2$ or O.

[18]

The present invention relates to the preparation method according to [1] above, wherein the general formula (I) is a compound represented by:

[Chemical Formula 11]

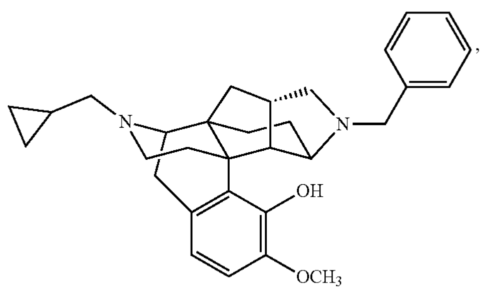

the general formula (II) is a compound represented by:

[Chemical Formula 12]

(III)

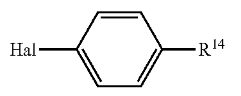

wherein $R^{14}$ represents a hydrogen atom or a tert-butyl group, and the general formula (III) is a morphinan derivative represented by:

[Chemical Formula 13]

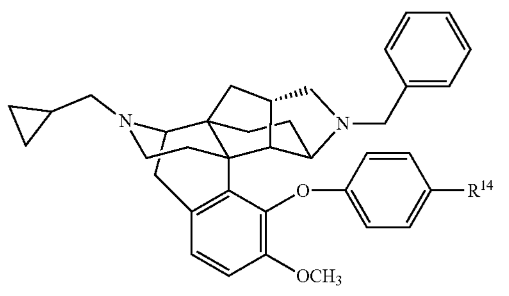

wherein $R^{14}$ represents a hydrogen atom or a tert-butyl group.

[19]

The present invention relates to the preparation method according to any one of [1] to [18] above, wherein the monovalent copper compound is at least one selected from the group consisting of cuprous chloride, cuprous bromide, cuprous iodide, cuprous oxide, and a cuprous complex.

[20]

The present invention relates to the preparation method according to any one of [1] to [18] above, wherein the monovalent copper compound is cuprous iodide or cuprous oxide.

[21]

The present invention relates to the preparation method according to any one of [1] to [20] above, wherein the monovalent copper compound is used in an amount of 0.01 to 2.0 equivalents relative to the compound represented by the general formula (I).

[22]

The present invention relates to the preparation method according to any one of [1] to [21] above, wherein the reaction is carried out in the presence of a monovalent copper compound and zero-valent metallic copper.

[23]

The present invention relates to the preparation method according to [22] above, wherein the zero-valent metallic copper is used in an amount of 0.01 to 2.0 equivalents relative to the compound represented by the general formula (I).

[24]

The present invention relates to the preparation method according to [22] or [23] above, wherein a conversion molar ratio of the monovalent copper compound to the zero-valent metallic copper (monovalent copper:zero-valent copper) is 1:0.2 to 1:6.

[25]

The present invention relates to the preparation method according to any one of [1] to [21] above, wherein the reaction is carried out in the absence of zero-valent metallic copper and in the presence of a monovalent copper compound.

[26]

The present invention relates to the preparation method according to any one of [1] to [25] above, wherein the organic solvent is an aprotic polar solvent.

[27]

The present invention relates to the preparation method according to [26] above, wherein the aprotic polar solvent is at least one selected from the group consisting of pyridine and dimethyl sulfoxide.

[28]

The present invention relates to the preparation method according to any one of [1] to [27] above, wherein the base is a salt of an alkali metal.

[29]

The present invention relates to the preparation method according to [28] above, wherein the salt of an alkali metal is at least one selected from the group consisting of a carbonate, a hydrogen carbonate, a phosphate, and a hydrogen phosphate.

[30]

The present invention relates to the preparation method according to any one of [1] to [29] above, wherein the reaction temperature is 50° C. to 150° C.

[31]

The present invention relates to the preparation method according to any one of [1] to [30] above, wherein the monovalent copper compound is powdered cuprous oxide and has a powder particle size of 10 to 100 nm.

Advantageous Effects of Invention

According to the present invention, there is an advantage that a morphinan derivative can be phenol-etherified with a high conversion rate and a high purity. Therefore, a morphinan derivative having a diaryl ether skeleton can be industrially advantageously prepared by the preparation method of the present invention.

DESCRIPTION OF EMBODIMENTS

Hereinafter, meanings of terms as used herein will be described, and the present invention will be described in more detail. The following description of terms does not limit the present invention.

The term "$C_{1-10}$ alkyl group" refers to a linear or branched acyclic saturated hydrocarbon having 1 to 10 carbon atoms. The alkyl group contains preferably 1 to 6 carbon atoms, and more preferably 1 to 4 carbon atoms. Examples of the alkyl group include a methyl group, an ethyl group, a propyl group, an isopropyl group, a butyl group, a tert-butyl group, a pentyl group, a neopentyl group, and a hexyl group.

The term "$C_{2-6}$ alkenyl group" refers to a linear or branched acyclic unsaturated hydrocarbon having one or more carbon-carbon double bonds and 2 to 6 carbon atoms. Examples of the alkenyl group include an ethenyl group, an allyl group, a 1-propen-2-yl group, a 2-propen-1-yl group, a 1,3-butadien-1-yl group, and a 1,3-butadien-2-yl group. The alkenyl group is preferably a $C_{2-4}$ alkenyl group having 2 to 4 carbon atoms.

The term "$C_{3-6}$ cycloalkyl group" refers to a saturated monocyclic or polycyclic hydrocarbon group having 3 to 6 carbon atoms, and the polycyclic hydrocarbon group may have a spiro ring, a fused ring, and a crosslinked ring. Examples of the monocyclic cycloalkyl group include a cyclopropyl group, a cyclobutyl group, a cyclopentyl group, and a cyclohexyl group.

Examples of the spiro ring in the polycyclic hydrocarbon group include a spiro[2.2]pentyl group, a spiro[2.3]hexyl group, a spiro[3.3]heptyl group, a spiro[3.5]nonyl group, and a spiro[4.5]decanyl group.

Examples of the fused ring in the polycyclic hydrocarbon group include a bicyclo[4.2.0]octyl group, a bicyclo[3.2.0] heptyl group, a decahydronaphthyl group, and an octahydroindenyl group.

Examples of the crosslinked ring in the polycyclic hydrocarbon group include a norbornyl group, a bicyclo[2.2.2] octyl group, and an adamantyl group.

The term "$C_{3-6}$ cycloalkyl $C_{1-6}$ alkyl group" refers to a group in which the alkyl group having 1 to 6 carbon atoms is substituted with the cycloalkyl group. Examples of the cycloalkylalkyl group include a cyclopropylmethyl group, a cyclopropylethyl group, a cyclopropylpropyl group, a cyclobutylmethyl group, a cyclobutylethyl group, a cyclobutylpropyl group, a cyclopentylmethyl group, a cyclopentylethyl group, a cyclopentylpropyl group, a cyclohexylmethyl group, a cyclohexylethyl group, and a cyclohexylpropyl group.

The term "$C_{6-10}$ aryl group" refers to a monocyclic or polycyclic aromatic hydrocarbon having 6 to 10 carbon atoms and having at least partially aromatic ring structure. Examples of the aryl group include a phenyl group, a naphthyl group, an indanyl group, an indenyl group, and an azulenyl group.

The term "heteroaryl group" refers to a monocyclic or polycyclic heterocyclic aromatic ring that is monocyclic or polycyclic and contains at least one heteroatom selected from a nitrogen atom, an oxygen atom and a sulfur atom, the nitrogen atom and the sulfur atom being optionally oxidized to various oxidation states.

Examples of the monocyclic heteroaryl group include a 5-membered ring heteroaryl group such as a furanyl group, a thienyl group, a pyrrolyl group, an imidazolyl group, a pyrazolyl group, an oxazolyl group, an isooxazolyl group, a thiazolyl group, an isothiazolyl group, a triazolyl group, or a tetrazolyl group; and a 6-membered ring heteroaryl group such as a pyridyl group, a pyridazinyl group, a pyrazinyl group, or a pyrimidyl group.

Examples of the polycyclic heteroaryl group include polycyclic heteroaryl groups such as a quinoline group, an isoquinolyl group, a quinazolyl group, a quinoxalyl group, an indolyl group, an indazolyl group, a benzoimidazolyl group, a benzofuranyl group, a benzothienyl group, a benzoxazolyl group, a benzothiazolyl group, an imidazolypyridinyl group, and a pyrazolopyridinyl group.

The term "heteroarylalkyl group" refers to a group in which the alkyl group is substituted with the heteroaryl group. Examples of the heteroarylalkyl group include a furanylmethyl group, a pyridylmethyl group, and a quinolylmethyl group.

The term "aralkyl group" refers to a group in which the alkyl is substituted with an aryl group such as a phenyl group. Examples of the aralkyl group include benzyl, phenethyl, and phenylpropyl.

The term "acyl group" is a carbonyl having a substituent and refers to an alkanoyl group, an aroyl group, and the like. The alkanoyl group includes —C(O)— the alkyl, —C(O)— the cycloalkyl, and —C(O)— the aralkyl, the aroyl group includes —C(O)— the aryl and —C(O)— the heteroaryl, and the alkyl, the aryl, or the like may have a substituent. Examples of the acyl group include a formyl group; a $C_{2-6}$ alkanoyl group such as an acetyl group, a propionyl group, a butanoyl group, a pentanoyl group, or a hexanoyl group; a $C_{4-7}$ cycloalkanecarbonyl group such as a cyclopropanecarbonyl group, a cyclobutanecarbonyl group, or a cyclopentanecarbonyl group; an aroyl group such as a benzoyl group or a naphthoyl group; and a 5- or 6-membered heteroaroyl group such as a furoyl group, a thiophenecarbonyl group, a nicotinoyl group, or an isonicotinoyl group.

Examples of the pyridine 1-oxide carbonyl include pyridine 1-oxide-2-carbonyl, pyridine 1-oxide-3-carbonyl, and pyridine 1-oxide-4-carbonyl, and examples of the pyridin-2(1H)-one carbonyl include pyridin-2(1H)-one-3-carbonyl, pyridin-2(1H)-one-4-carbonyl, pyridin-2(1H)-one-5-carbonyl, and pyridin-2(1H)-one-6-carbonyl.

The term "halogen atom" refers to a fluorine atom, a chlorine atom, a bromine atom, or an iodine atom.

The term "amino protecting group" refers to a group that is suitable for protecting an amino group against chemical reactions and that can be removed after the desired chemical reaction has been carried out. Examples of the amino protecting group include a methoxymethyl group, a benzyl group, a formyl group, an acetyl group, a trifluoroacetyl group, a tert-butoxycarbonyl group, an allyloxycarbonyl group, a 2,2,2-trichloroethoxycarbonyl group, a benzyloxycarbonyl group, a 9-fluorenylmethyloxycarbonyl group, a p-toluenesulfonyl group, and a 2-nitrobenzenesulfonyl group, but are not limited thereto. For example, a protecting group described in Green's Protective Groups in Organic Synthesis, 5th ed., and the like can be used.

The term "hydroxy protecting group" refers to a group that is suitable for protecting a hydroxy group against chemical reactions and that can be removed after the desired chemical reaction has been carried out. Examples of the hydroxy protecting group include an alkyl group that may have a substituent such as a methyl group, a methoxymethyl group, or an ethoxyethyl group, an aralkyl group that may have a substituent such as a benzyl group, a 4-methoxybenzyl group, or a trityl group, an alkanoyl group such as an acetyl group, and a silyl group having a substituent such as a trimethylsilyl group or a tert-butyldimethylsilyl group, but are not limited thereto. For example, a protecting group described in Green's Protective Groups in Organic Synthesis, 5th ed. and the like can be used.

The term "optionally having a substituent" refers to being unsubstituted or substituted with an arbitrary substituent. The number of substituents and substitution position are not limited, but in a case where two or more substituents are present, these substituents may be the same or different.

The term "arbitrary substituent" may be any group other than a hydrogen atom, and examples of typical substituents include, but are not limited to, an alkyl group, an alkenyl group, an alkynyl group, an alkoxy group, a hydroxyl group, a cyano group, a nitro group, a halogen group, a carboxyl group, an alkoxycarbonyl group, an acyl group, a mercapto group, an alkylthio group, a sulfonyl group, an alkylsulfonyl group, a sulfinyl group, an alkylsulfinyl group, a sulfonamide group, an alkanesulfonamide group, a carbamoyl group, a thiocarbamoyl group, an aminocarbonyl group, an aminosulfonyl group, an amino group, a mono- or dialkylamino group, a carbonylamino group, an acyloxy group, an oxo group, a thioxo group, a cycloalkyl group, a heterocycloalkyl group, an aryl group, a heteroaryl group, an aralkyl group, an aryloxy group, a heteroaryloxy, an aralkyloxy group, an arylthio group, a heteroarylthio group, and an aralkylthio group.

In the preparation method of the present invention, a diaryl ether derivative of morphinan represented by general formula (III) can be prepared using a morphinan derivative represented by general formula (I) and a halobenzene derivative represented by general formula (II).

[Chemical Formula 14]

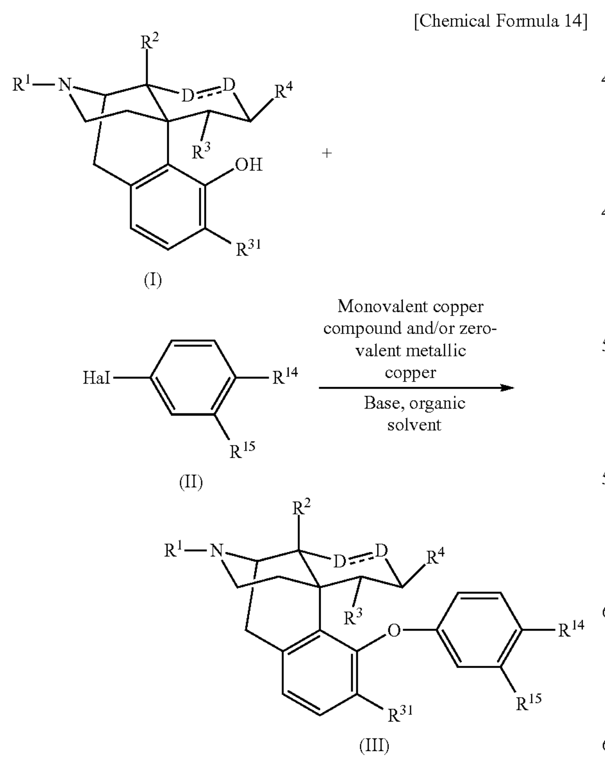

(I)

(II)

(III)

The morphinan derivative represented by the general formula (I) can be prepared by the method described in Patent Literature 1 or a method equivalent thereto. In addition, a commercially available product (for example, thebainone or ketorphanol) can be adjusted by a known method and used.

As the halobenzene derivative represented by the general formula (II), a commercially available halobenzene derivative can be used, and the halobenzene derivative can also be prepared by a method well known to those skilled in the art.

As the "base" added to the reaction, alkali metal carbonates such as sodium carbonate, potassium carbonate, and cesium carbonate, or hydrogen carbonates; alkali metal phosphates such as potassium phosphate, and hydrogen phosphates; amines such as trimethylamine and triethylamine; or metal halides such as potassium fluoride and cesium fluoride, or the like can be used. Potassium carbonate, sodium carbonate, or potassium phosphate is preferable, and potassium phosphate is more preferable.

The copper catalyst in the present invention is not particularly limited, and a known catalyst used for the Ullmann reaction can be used.

Examples of the "monovalent copper compound" include cuprous chloride, cuprous bromide, copper iodide, cuprous oxide, and a cuprous complex. CuI (copper iodide) or $Cu_2O$ (copper(I) oxide) is preferable because the ligand does not become an impurity after the reaction and purification becomes easy. $Cu_2O$ that is a so-called nanoparticle having a particle size of 10 to 100 nm, 30 to 70 nm, and particularly 50 nm is preferable.

Examples of the cuprous complex include pyridine-2-carboxylic acid, dipivaloylmethane, N,N-dimethylglycine, 1,10-phenanthroline, proline, 2-thiophenecarboxylic acid, 2,2'-bipyridyl, ethyl 2-oxocyclohexanecarboxylate, 3,4,7,8-tetramethyl-1,10-phenanthroline, and N,N-dimethylethylenediamine.

Examples of the "zero-valent copper" include metallic copper and a copper complex. Examples of the shape of the metallic copper include a powder shape, a mesh shape, a rod shape, a plate shape, and a pot shape, and a powder shape having a relatively larger specific surface area is preferable. Regarding the powder shape, generally commercially available products can be used as they are.

The monovalent copper compound can be used in an amount of, for example, 0.01 to 2.0 equivalents, 0.02 to 2.0 equivalents, 0.05 to 1.5 equivalents, 0.1 to 1.0 equivalents, 0.15 to 1.0 equivalents, 0.2 to 1.0 equivalents, 0.25 to 1.0 equivalents, 0.3 to 1.0 equivalents, or 0.5 to 1.0 equivalents relative to the compound represented by the general formula (I).

The zero-valent metallic copper can be used in an amount of, for example, 0.01 to 2.0 equivalents, 0.1 to 1.5 equivalents, 0.2 to 1.0 equivalents, 0.45 to 1.0 equivalents, 0.5 to 1.0 equivalents, 0.6 to 1.0 equivalents, or 0.85 to 1.0 equivalents relative to the compound represented by the general formula (I).

When the monovalent copper compound and the zero-valent metallic copper are simultaneously used, they can be used at a conversion molar ratio (monovalent copper:zero-valent copper) of, for example, 1:0.2, 1:0.45, 1:0.5, 1:1, 1:1.33, 1:2, 1:4, 1:5.67, or 1:6, and more preferably 1:4.

The solvent used in the reaction is not particularly limited as long as it is an organic solvent, but an aprotic polar solvent is preferable. Examples of the aprotic polar solvent include tetrahydrofuran (THF), 2-methyltetrahydrofuran (2-MeTHF), formamide, N-methylformamide, dimethylformamide (DMF), N-methylacetamide, dimethyl atacemide (DMAC), N-methylpyrrolidinone (NMP), dimethyl sulfoxide (DMSO), acetonitrile, propionitrile, acetone, ethyl methyl ketone, methyl acetate, ethyl acetate, sulfolane, tetramethylurea, hexamethylphosphoramide, nitromethane, nitrobenzene, toluene, xylene, and pyridine. These can be used alone or in combination of two or more. In the present invention, DMSO and pyridine are preferable, and pyridine is more preferable.

The reaction temperature varies depending on the type of a raw material compound, a reaction reagent, or a solvent used, but the reaction can be carried out, for example, in the range of room temperature to the boiling point of the solvent, and, for example, at 20° C. to 200° C., 25° C. to 200° C., 50° C. to 180° C., 50° C. to 150° C., 80° C. to 150° C., 100° C. to 130° C., and more preferably 110° C. to 120° C.

EXAMPLES

Hereinafter, the present invention will be further clarified by way of Reference Examples and Examples, but the present invention is not limited to these examples.

Compounds in Examples and compounds in Reference Examples were named by converting a structural formula drawn using ChemDraw ver. 14 or ver. 18 manufactured by Cambridge Software Corporation as an English name by a naming algorithm mounted on the software and then translating the English name into Japanese.

The identification of a product was determined by HPLC analysis in agreement with the elution time of a reference standard. In addition, the conversion rate and the purity of a reaction were calculated from the peak areas of remaining raw materials and a product.

<HPLC Conditions>

Column: ZORBAX Bonus-RP (Agilent), 4.6×150 mm, particle size of 3.5 μm

Column temperature: 35° C.

Detection: 204 nm (DAD)

Flow rate: 1.0 mL/min

Mobile phase: solution A=0.05% aqueous TFA solution, solution B=0.05% TFA acetonitrile Gradient Conditions:

0 minutes to 12 minutes, solution A: solution B=95:5 to solution A: solution B=10:90 (gradient)

12 minutes to 16 minutes, solution A: solution B=10:90 (continuation)

Retention Time:

(1S,3aR,5aS,6R,11bS,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indol-11-ol, about 5.4 minutes (1S,3aR,5aS,6R,11bS,11cS)-3-benzyl-11-(4-(tert-butyl)phenoxy)-14-(cyclopropylmethyl)-10-methoxy-2,3,3a,4,5,6,7,11c-octahydro-1H-6,11b-(epiminoethano)-1,5a-methanonaphtho[1,2-e]indole, 7.2 to 7.3 minutes 1S,3aR,5aS,6R,11bS,11cS)-3-benzyl-11-phenoxy-14-(cyclopropylmethyl)-11-phenoxy-10-methoxy-11-phenoxy-2,3,3a,4,5,6,7,11c-octahydro-1H-6,11b-(epiminoethano)-1,5a-methanonaphtho[1,2-e]indole, about 6.3 minutes Synthesis of (1S,3aR,5aS,6R,11bS,11cS)-3-benzyl-11-(4-(tert-butyl)phenoxy)-14-(cyclopropylmethyl)-10-methoxy-2,3,3a,4,5,6,7,11c-octahydro-1H-6,11b-(epiminoethano)-1,5a-methanonaphtho[1,2-e]indole

[Chemical Formula 15]

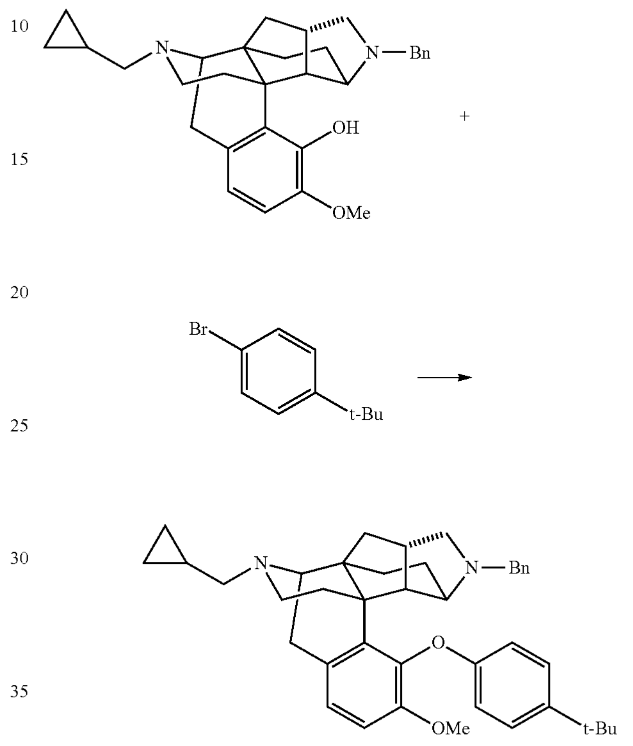

Example 1

(1S,3aR,5aS,6R,11bS,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indol-11-ol (286 g, 1 equivalent) was dissolved in pyridine (4.3 L), and the mixture was bubbled with nitrogen for 10 minutes. Tripotassium phosphate (259 g, 2 equivalents) was added, and after replacement with nitrogen 3 times, the mixture was bubbled for 15 minutes. After stirring at 95 to 105° C. for 1 hour, a copper powder (39.0 g, 1 equivalent), cuprous oxide (average particle size of 50 nm, 22.0 g, 0.25 equivalents), and 4-tert-butylbromobenzene (650 g, 5 equivalents) were added at 95 to 105° C. while stirring, and then the mixture was stirred at 110 to 120° C. for 16 hours. When HPLC of the reaction solution was measured, the conversion rate was 99.35% and the purity was 96.14%.

The reaction mixture was cooled to room temperature, and then filtered through a silica gel pad to remove insoluble matters. The filtrate was concentrated, and then the silica gel pad was washed twice (4.3 L, 430 mL) with methyl tert-butyl ether, followed by addition to the organic layer. The combined organic layers were then washed 3 times (2.86 L×3) with 8.3% to 9.3% aqueous ammonia. The aqueous layers were combined and extracted once (1.43 L) with methyl tert-butyl ether. The organic layers were combined and washed 3 times (2.86 L×3) with water. Water (4.3 L) was added to the organic layer, 4 N hydrochloric acid was added thereto to adjust the pH of the aqueous layer to 2 to 3, and the organic layer was separated.

The aqueous layer was washed twice (1.43 L×2) with methyl tert-butyl ether and concentrated to remove residual methyl tert-butyl ether.

To the aqueous layer, 25 to 28% aqueous ammonia was added to adjust the pH to 9, and then the mixture was stirred at room temperature for 30 minutes, and the precipitate was collected by filtration and washed with water (858 mL). The obtained solid was dried to obtain the title compound (315 g, yield: 81.63%, purity: 92.90%).

$^1$H-NMR (400 MHz, $CDCl_3$): δ 7.10-7.35 (m, 7H), 6.97 (d, 1H, J=8 Hz), 6.77 (d, 1H, J=8 Hz), 6.67 (d, 2H, J=8H z), 3.70 (d, 1H, J=13 Hz), 3.68 (s, 3H), 3.55 (d, 1H, J=13 Hz), 2.90-3.20 (m, 6H), 2.60-2.70 (m, 1H), 2.46 (dd, 1H, J=4.12 Hz), 2.29 (d, 2H, J=6 Hz), 1.99 (dt, 1H, J=3.13 Hz), 1.75 (dt, 1H, J=5.13 Hz), 1.50-1.65 (m, 3H), 1.30 (s, 9H), 1.20-1.35 (m, 1H), 1.10-1.20 (m, 1H), 1.00-1.10 (m, 2H), 0.70-0.85 (m, 2H), 0.40-0.50 (m, 2H), 0.00-0.15 (m, 2H).

Example 2

Pyridine (4 mL) was added to a reactor, and the mixture was bubbled with nitrogen for 10 minutes. (1S,3aR,5aS,6R, 11bS,11cS)-3-benzyl-14-(cyclopropylmethyl)-10-methoxy-2,3,3a,4,5,6,7,11c-octahydro-1H-6,11b-(epiminoethano)-1, 5a-methanonaphtho[1,2-e]indol-11-ol (0.4 g, 1 equivalent) was added to the reactor and dissolved. Tripotassium phosphate (0.36 g, 2 equivalents) was added, and after replacement with nitrogen 3 times, the mixture was bubbled for 15 minutes. After stirring at 95 to 105° C. for 1 hour, cuprous oxide (0.12 g, 1 equivalent) and 4-tert-butylbromobenzene (0.91 g, 5 equivalents) were added at 95 to 105° C., and then the mixture was stirred at 110 to 120° C. for 16 hours. When HPLC of the reaction solution was measured, the conversion rate was 100% and the purity was 76.99%.

Example 3

Pyridine (10 mL) was added to a reactor, and the mixture was bubbled with nitrogen for 10 minutes. (1S,3aR,5aS,6R, 11bS,11cS)-3-benzyl-14-(cyclopropylmethyl)-10-methoxy-2,3,3a,4,5,6,7,11c-octahydro-1H-6,11b-(epiminoethano)-1, 5a-methanonaphtho[1,2-e]indol-11-ol (1.0 g, 1 equivalent) was added to the reactor and dissolved. Tripotassium phosphate (0.90 g, 2 equivalents) was added, and after replacement with nitrogen 3 times, the mixture was bubbled for 15 minutes. After stirring at 95 to 105° C. for 1 hour, cuprous oxide (61.3 mg, 0.2 equivalents) and 4-tert-butylbromobenzene (2.27 g, 5 equivalents) were added at 95 to 105° C., and then the mixture was stirred at 110 to 120° C. for 16 hours. When HPLC of the reaction solution was measured, the conversion rate was 92.8% and the purity was 76.71%.

Example 4

Pyridine (20 mL) was added to a reactor, and the mixture was bubbled with nitrogen for 10 minutes. (1S,3aR,5aS,6R, 11bS,11cS)-3-benzyl-14-(cyclopropylmethyl)-10-methoxy-2,3,3a,4,5,6,7,11c-octahydro-1H-6,11b-(epiminoethano)-1, 5a-methanonaphtho[1,2-e]indol-11-ol (2.0 g, 1 equivalent) was added to the reactor and dissolved. Tripotassium phosphate (1.80 g, 2 equivalents) was added, and after replacement with nitrogen 3 times, the mixture was bubbled for 15 minutes. After stirring at 95 to 105° C. for 1 hour, a copper powder (54.6 mg, 0.2 equivalents), cuprous oxide (92 mg, 0.15 equivalents), and 4-tert-butylbromobenzene (4.54 g, 5 equivalents) were added at 95 to 105° C., and then the mixture was stirred at 110 to 120° C. for 16 hours. When HPLC of the reaction solution was measured, the conversion rate was 99.18% and the purity was 83.33%.

Example 5

Pyridine (20 mL) was added to a reactor, and the mixture was bubbled with nitrogen for 10 minutes. (1S,3aR,5aS,6R, 11bS,11cS)-3-benzyl-14-(cyclopropylmethyl)-10-methoxy-2,3,3a,4,5,6,7,11c-octahydro-1H-6,11b-(epiminoethano)-1, 5a-methanonaphtho[1,2-e]indol-11-ol (2.0 g, 1 equivalent) was added to the reactor and dissolved. Tripotassium phosphate (1.80 g, 2 equivalents) was added, and after replacement with nitrogen 3 times, the mixture was bubbled for 15 minutes. After stirring at 95 to 105° C. for 1 hour, a copper powder (54.6 mg, 0.2 equivalents), copper iodide (0.81 g, 1 equivalent), and 4-tert-butylbromobenzene (4.54 g, 5 equivalents) were added at 95 to 105° C., and then the mixture was stirred at 110 to 120° C. for 16 hours. When HPLC of the reaction solution was measured, the conversion rate was 92.4% and the purity was 84.66%. A copper powder (68 mg, 0.25 equivalents) was added to the reactor, and then the mixture was stirred at 110 to 120° C. for 4 hours. When HPLC of the reaction solution was measured, the conversion rate was 99.1% and the purity was 88.78%.

Example 6

Pyridine (50 mL) was added to a reactor, and the mixture was bubbled with nitrogen for 10 minutes. (1S,3aR,5aS,6R, 11bS,11cS)-3-benzyl-14-(cyclopropylmethyl)-10-methoxy-2,3,3a,4,5,6,7,11c-octahydro-1H-6,11b-(epiminoethano)-1, 5a-methanonaphtho[1,2-e]indol-11-ol (5.0 g, 1 equivalent) was added to the reactor and dissolved. Tripotassium phosphate (4.51 g, 2 equivalents) was added, and after replacement with nitrogen 3 times, the mixture was bubbled for 15 minutes. After stirring at 95 to 105° C. for 1 hour, a copper powder (0.41 g, 0.6 equivalents), cuprous oxide (0.23 g, 0.15 equivalents), and 4-tert-butylbromobenzene (11.33 g, 5 equivalents) were added at 95 to 105° C., and then the mixture was stirred at 110 to 120° C. for 16 hours. When HPLC of the reaction solution was measured, the conversion rate was 90.20% and the purity was 85.54%. A copper powder (0.17 g, 0.25 equivalents) was added to the reactor, and then the mixture was stirred at 110 to 120° C. for 3 hours. When HPLC of the reaction solution was measured, the conversion rate was 93.58% and the purity was 86.93%. A copper powder (0.17 g, 0.25 equivalents) was added to the reactor, and then the mixture was stirred at 110 to 120° C. for 2 hours. When HPLC of the reaction solution was measured, the conversion rate was 97.88% and the purity was 91.27%.

The reaction mixture was cooled to room temperature, and then filtered through a silica gel pad to remove insoluble matters. The silica gel pad was washed with methyl tert-butyl ether (10 mL), followed by addition to the organic layer. Thereafter, the combined organic layers were concentrated to 5 to 10 mL, and methyl tert-butyl ether (75 mL) was added thereto to form a dark brown suspension. Thereafter, the organic layer was washed with 13% to 14% aqueous ammonia 3 times (50 mL×3). The aqueous layers were combined and extracted (25 mL) with methyl tert-butyl ether. The organic layers were combined and washed with water (50 mL). Water (75 mL) was added to the organic layer, 4 N hydrochloric acid was added thereto to adjust the pH of the aqueous layer to 3 to 4, and the organic layer was separated.

The aqueous layer was washed with methyl tert-butyl ether (25 mL) and concentrated to remove residual methyl tert-butyl ether. After the aqueous layer was heated to 50 to 55° C., 25 to 28% ammonia water was added thereto to adjust the pH to 8 to 9, and then the temperature was returned to room temperature, and the precipitate was collected by filtration, then washed with water (10 mL) and dried to obtain a yield of the title compound (5.2 g, yield: 81.98%, purity: 93.95%).

Example 7

Pyridine (4 mL) was added to a reactor, and the mixture was bubbled with nitrogen for 10 minutes. (1S,3aR,5aS,6R,11bS,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indol-11-ol (0.4 g, 1 equivalent) was added to the reactor and dissolved. Tripotassium phosphate (0.36 g, 2 equivalents) was added, and after replacement with nitrogen 3 times, the mixture was bubbled for 15 minutes. After stirring at 95 to 105° C. for 1 hour, 2-thiophenecarboxylic acid (11 mg, 0.1 equivalents), copper iodide (16 mg, 0.1 equivalent), and 4-tert-butylbromobenzene (0.91 mg, 5 equivalents) were added at 95 to 105° C., and then the mixture was stirred at 110 to 120° C. for 16 hours. When HPLC of the reaction solution was measured, the conversion rate was 89.8% and the purity was 75.8%.

Example 8

DMSO (2 mL) was added to a reactor, and the mixture was bubbled with nitrogen for 10 minutes. (1S,3aR,5aS,6R,11bS,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indol-11-ol (0.2 g, 1 equivalent) was added to the reactor and dissolved. Tripotassium phosphate (0.18 g, 2 equivalents) was added, and after replacement with nitrogen 3 times, the mixture was bubbled for 15 minutes. After stirring at 95 to 105° C. for 1 hour, copper(I) 2-thiophenecarboxylate (8.1 mg, 0.1 equivalents) and 4-tert-butylbromobenzene (0.45 g, 5 equivalents) were added at 95 to 105° C., and then the mixture was stirred at 110 to 120° C. for 16 hours. When HPLC of the reaction solution was measured, the conversion rate was 95.92% and the purity was 45.60%.

Synthesis of (1S,3aR,5aS,6R,11bS,11cS)-3-benzyl-11-phenoxy-14-(cyclopropylmethyl)-11-phenoxy-10-methoxy-11-phenoxy-2,3,3a,4,5,6,7,11c-octahydro-1H-6,11b-(epiminoethano)-1,5a-methanonaphtho[1,2-e]indole

[Chemical Formula 16]

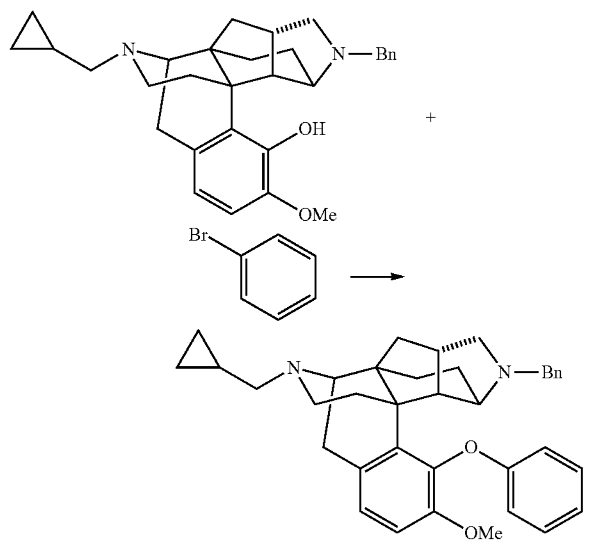

Example 9

Pyridine (20 mL) was added to a reactor, and the mixture was bubbled with nitrogen for 10 minutes. (1S,3aR,5aS,6R,11bS,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indol-11-ol (2.0 g, 1 equivalent) was added to the reactor and dissolved. Potassium tert-butoxide (0.48 g, 1 equivalent) and tripotassium phosphate (0.9 g, 1 equivalent) were added, and after replacement with nitrogen 3 times, the mixture was bubbled for 15 minutes. After stirring at 95 to 105° C. for 1 hour, a copper powder (54.6 mg, 0.2 equivalents), cuprous oxide (92 mg, 0.15 equivalents), and bromobenzene (3.33 g, 5 equivalents) were added at 95 to 105° C., and then the mixture was stirred at 110 to 120° C. for 16 hours. When HPLC of the reaction solution was measured, the conversion rate was 99.6% and the purity was 95.61%.

Example 10

Pyridine (50 mL) was added to a reactor, and the mixture was bubbled with nitrogen for 10 minutes. (1S,3aR,5aS,6R,11bS,11cS)-3-benzyl-14-(cyclopropylmethyl)-10-methoxy-2,3,3a,4,5,6,7,11c-octahydro-1H-6,11b-(epiminoethano)-1,5a-methanonaphtho[1,2-e]indol-11-ol (5.0 g, 1 equivalent) was added to the reactor and dissolved. Tripotassium phosphate (4.51 g, 2 equivalents) was added, and after replacement with nitrogen 3 times, the mixture was bubbled for 15 minutes. After stirring at 95 to 105° C. for 1 hour, a copper powder (0.68 g, 1 equivalent), cuprous oxide (0.38 g, 0.25 equivalents), and bromobenzene (8.35 g, 5 equivalents) were added at 95 to 105° C., and then the mixture was stirred at 110 to 120° C. for 16 hours. When HPLC of the reaction solution was measured, the conversion rate was 99.4% and the purity was 92.88%.

INDUSTRIAL APPLICABILITY

According to the present invention, there is provided an industrial method for preparing a morphinan derivative having a diaryl ether skeleton.

The invention claimed is:

1. A method for preparing a morphinan derivative, the method comprising:

reacting a compound represented by the following general formula (I):

(I)

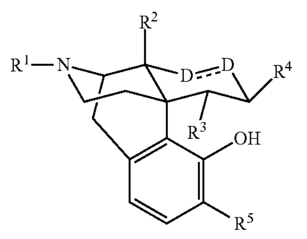

wherein $R^1$ represents a hydrogen atom, a $C_{1-10}$ alkyl group optionally having a substituent, a $C_{3-6}$ cycloalkyl $C_{1-6}$ alkyl group optionally having a substituent, an aralkyl group optionally having a substituent, a heteroarylalkyl group optionally having a substituent, a $C_{3-6}$ cycloalkyl group optionally having a substituent, a $C_{6-10}$ aryl group optionally having a substituent, a heteroaryl group optionally having a substituent, a $C_{2-6}$ alkenyl group optionally having a substituent, or an amino protecting group, $R^2$, $R^3$, and $R^4$ are the same or different and each represent a hydrogen atom or an substituent, or with respect to the moiety:

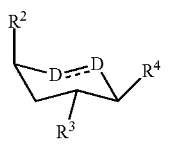

of the general formula (I), $R^2$ and $R^4$ are bonded to each other to represent:

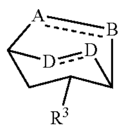

wherein a double line consisting of a solid line and a broken line represents a single bond or a double bond, wherein, when the double line consisting of a solid line and a broken line between A and B is a single bond, then A and B are the same or different and each represent $CR^6R^7$, C═O, or $NR^8$, wherein $R^6$ and $R^7$ are the same or different and each represent a hydrogen atom, —C(═O)—$R^9$, or —$CR^{10}$(OH)—$R^{11}$, and $R^8$ to $R^{11}$ each represent a hydrogen atom or an arbitrary substituent, and when the double line consisting of a solid line and a broken line between A and B is a double bond, then A and B are the same or different and each represent $CR^6$ or N, wherein $R^6$ and $R^9$ to $R^{11}$ each represent the same as mentioned above, and when the double line consisting of a solid line and a broken line between D and D is a single bond, then D represents $CH_2$, and when the double line consisting of a solid line and a broken line between D and D is a double bond, then D represents CH, or $R^2$ to $R^4$ are bonded to each other to represent:

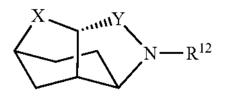

wherein X represents $CH_2$, $NR^8$ ($R^8$ represents a hydrogen atom or an arbitrary substituent), or O, Y represents $CH_2$ or C═O, and $R^{12}$ represents an amino protecting group or an acyl group, and $R^5$ represents a hydrogen atom, a hydroxy group, or —$OR^{13}$ ($R^{13}$ represents a hydroxy protecting group), with a compound represented by the following general formula (II):

(II)

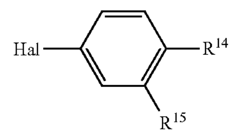

wherein $R^{14}$ and $R^{15}$ are the same or different and each represent a hydrogen atom or an arbitrary substituent, and Hal represents a halogen atom, in an organic solvent in the presence of a base, a monovalent copper compound, and a zero-valent metallic copper, wherein the monovalent copper compound is at least one selected from the group consisting of cuprous chloride, cuprous bromide, cuprous iodide and cuprous oxide, and the zero-valent metallic copper is copper powder, and the morphinan derivative being represented by the following general formula (III):

[Chemical Formula 6]

(III)

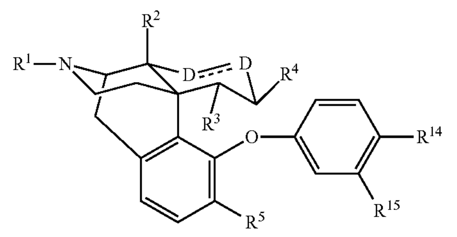

wherein $R^1$ to $R^5$, $R^{14}$, $R^{15}$, and D each represent the same as mentioned above.

2. The preparation method according to claim 1, wherein the general formula (I) is a compound represented by the following general formula (IV):

(IV)

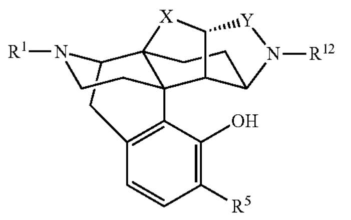

wherein $R^1$, $R^5$, $R^{12}$, X, and Y each represent the same as in claim 1, and the general formula (III) is a morphinan derivative represented by the following general formula (V):

(V)

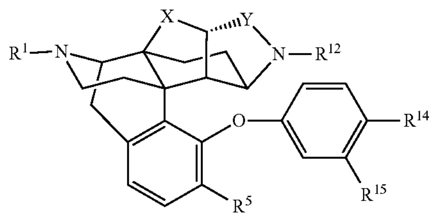

wherein $R^1$, $R^5$, $R^{12}$, $R^{14}$, $R^{15}$, X, and Y each represent the same as in claim 1.

3. The preparation method according to claim 1, wherein $R^1$ is a methyl group, a cyclopropylmethyl group, a cyclobutylmethyl group, a benzyl group, or an allyl group.

4. The preparation method according to claim 1, wherein $R^1$ is a cyclopropylmethyl group.

5. The preparation method according to claim 1, wherein $R^5$ is a hydroxy group or —$OR^{13}$ ($R^{13}$ represents a hydroxy protecting group).

6. The preparation method according to claim 1, wherein $R^5$ is —$OR^{13}$, and $R^{13}$ is a methyl group, a benzyl group, or a tert-butyldimethylsilyl group.

7. The preparation method according to claim 1, wherein $R^5$ is —$OR^{13}$, and $R^{13}$ is a methyl group.

8. The preparation method according to claim 1, wherein X is $CH_2$.

9. The preparation method according to claim 1, wherein Y is $CH_2$.

10. The preparation method according to claim 1, wherein $R^{12}$ is a benzyl group.

11. The preparation method according to claim 2, wherein $R^5$ is —$OR^{13}$, $R^{13}$ is a methyl group or another hydroxy protecting group, and X represents $CH_2$ or O.

12. The preparation method according to claim 2, wherein $R^1$ is a cyclopropylmethyl group or a methyl group, and X represents $CH_2$ or O.

13. The preparation method according to claim 1, wherein the general formula (I) is a compound represented by:

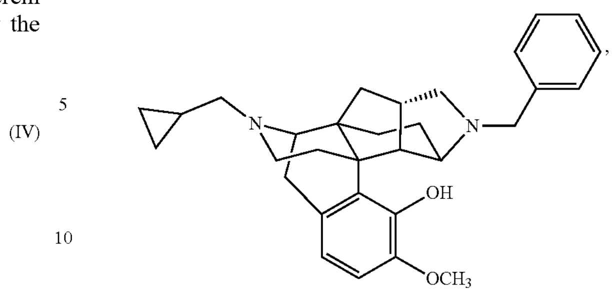

the general formula (II) is a compound represented by:

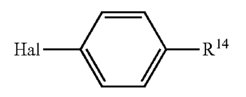

wherein $R^{14}$ represents a hydrogen atom or a tert-butyl group, and Hal represents a halogen atom, and the general formula (III) is a morphinan derivative represented by:

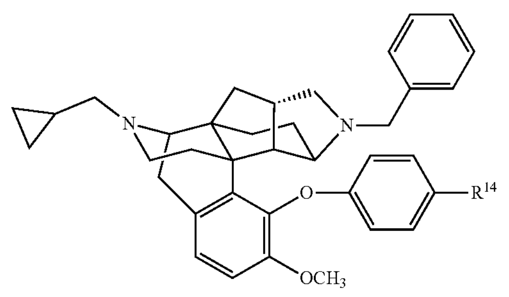

wherein $R^{14}$ represents a hydrogen atom or a tert-butyl group.

14. The preparation method according to claim 1, wherein the monovalent copper compound is used in an amount of 0.01 to 2.0 equivalents relative to the compound represented by the general formula (I).

15. The preparation method according to claim 1, wherein the zero-valent metallic copper is used in an amount of 0.01 to 2.0 equivalents relative to the compound represented by the general formula (I).

16. The preparation method according to claim 1, wherein a conversion molar ratio of the monovalent copper compound to the zero-valent metallic copper (monovalent copper: zero-valent copper) is 1:0.2 to 1:6.

17. The preparation method according to claim 1, wherein the organic solvent is an aprotic polar solvent.

18. The preparation method according to claim 17, wherein the aprotic polar solvent is at least one selected from the group consisting of pyridine and dimethyl sulfoxide.

19. The preparation method according to claim 1, wherein the base is a salt of an alkali metal.

20. The preparation method according to claim 19, wherein the salt of an alkali metal is at least one selected from the group consisting of a carbonate, a hydrogen carbonate, a phosphate, and a hydrogen phosphate.

21. The preparation method according to claim 1, wherein the reaction temperature is 50° C. to 150° C.

22. The preparation method according to claim 1, wherein the monovalent copper compound is powdered cuprous oxide and has a powder particle size of 10 to 100 nm.

* * * * *